United States Patent [19]
Strickland

[11] Patent Number: 5,846,797
[45] Date of Patent: Dec. 8, 1998

[54] COTTON TRANSFORMATION

[75] Inventor: Steven G. Strickland, Davis, Calif.

[73] Assignee: Calgene, Inc., Davis, Calif.

[21] Appl. No.: 539,176

[22] Filed: Oct. 4, 1995

[51] Int. Cl.$^6$ ............................ C12N 15/82; C12N 15/84; A01H 4/00; A01H 5/00
[52] U.S. Cl. ...................................... 435/172.3; 435/252.2; 435/419; 435/427; 435/430; 435/430.1; 435/431; 800/205; 800/DIG. 27; 800/DIG. 63
[58] Field of Search ........................... 435/172.3, 240.49, 435/240.5, 240.54, 252.2, 419, 427, 430, 430.1, 431; 800/205, DIG. 27, DIG. 63

[56] References Cited

U.S. PATENT DOCUMENTS

| | | | |
|---|---|---|---|
| 4,634,674 | 1/1987 | Shahin | 435/240 |
| 4,672,035 | 6/1987 | Davidonis | 435/240.4 |
| 4,945,050 | 7/1990 | Sanford et al. | 435/172.1 |
| 5,004,863 | 4/1991 | Umbeck | 800/205 |
| 5,159,135 | 10/1992 | Umbeck | 800/205 |
| 5,244,802 | 9/1993 | Rangan | 435/240.5 |
| 5,474,925 | 12/1995 | Maliyakal | 435/172.3 |

FOREIGN PATENT DOCUMENTS

| | | |
|---|---|---|
| WO 87/02701 | 7/1987 | WIPO . |
| WO 92/15675 | 9/1992 | WIPO . |

OTHER PUBLICATIONS

Derwent Abstract #95–250659: Hokko Chem Ind Co Ltd, XP002027343 & JP 07 155 081A, 20 Jun. 1995.
Derwent Abstract #87–325191: Mitsui Toatsu Chem Inc., XP002027344 & JP 62 232 312 A, 12 Oct., 1987.
Derwent Abstract #95–287845: Nissan Chem Ind Ltd, XP 002027345 & JP 07 184 496 A 25 Jul. 1995.
Derwent Abstract #88–193366: Norinsho KK, XP0020273546 & JP 63 129 930 A 2 Jun. 1988.
Derwent Abstract #95–299433: ZH Norin Suisan Sentan Gijutsu Sangyo, 1 Aug. 1995.
Troliner and Xhixian, *Plant Cell Reports 8:133–136 (1989)*.
Cousins, Y.L., et al., Transformation of an Australian Cotton Cultivar: Prospects for Cotton Improvement through Genetic Engineering *Aust. J. Plant Physiol. 18:481–494 (1991)*.
Trolinder and Goodin, "Somatic embryogenesis in Cotton (Gossypium), II. Requirements for embryo development and plant regeneration", *Plant Cell, Tissue and Organ Culture 12, 43–53 (1988)*.
Voo, et al., "Indirect Somatic Embryogenesis and Plant Recovery from Cotton (*Gossypium Hirsutim* L.)" *In Vitro Cell. Dev. Biol. 27P:117–12 (Jul. 1991)*.
Shang, et al., Buffer Capacity of Cotton Cells and Effects of Extracellular pH on Growth and Somatic Embryogenesis in Cotton Cell Suspensions:,*In Vitro Cell. Dev. Biol. 27P 147–15 (Jul. 1991)*.
Gawel, et al., "Somatic embryogenesis in two *Gossypium hirsutum* genotypes on semi–solid verus liquid proliferation media", *Plant Cell, Tissue and Organ Culture 23: 201–204 (1990)*.

Davidonis and Hamilton, "Plant Regeneration from Callus Tissue of *gossypium Hirsutum* L.", *Plant Sci. Letter* (1983) 32:89–93.
Shoemaker, et al., "Characterization of somatic embryogenesis and plant regeneration in cotton (*Gossypium hirsutum* L.)", *Plant Cell Reports,* (1986) 3:178–181.
Firoozabady et al., "Transformation of cotton (*Gossypium hirsutum* L.) by *Agrobacterium tumefaciens* and regeneration of transgenic plants" *Plant Molecular Biology,* (1987) 10:105–116.
Trolinder and Goodin, Somatic embryogenesis and plant regeneration in cotton (*Gossypium hirsutum* L.) *Plant Cell Reports* (1987) 6:231–234.
Trolinder and Goodin, "Somatic embryogenesis in cotton (Gossypium) I. Effects of source of explant and hormone regime", *Plant Cell, Tissue and Organ Culture* (1988) 12:31–42.
Finer, J.J., "Plant Regeneration from somatic embryogenic suspension cultures of cotton," *Plant Cell Reports,* (1987) 7:399–402.
Obeidy, A.A, Smith, M.A.L., In Vitro (1988) 27:45A.
Umbeck and Stewart, "Substitution of cotton Cytoplasms from Wild Diploid Specied for Cotton Germplasm Improvement", *Crop Science,* (1985) 25:1015–1019.
Umbeck et al., "Genetically Transformed Cotton (*Gossypium Hirsutum* L.) Plants", *Bio/Technology* (1987) 5:263–266.
Klein et al., "High–velocity microprojectiles for delivering nucleic acids into living cells", *Nature* (1988) 327:70–73.
Price and Smith (1983) in *Handbook of Plant Cell Culture,* pp. 487–510.
Mitten, "Somatic Embryogenesis in *Gossypium Hirsutum* L." *Beltwide Cotton Production Research Conference,* (1985) pp. 57–58.
Voo, et al., "Maturation of Somatic Embryos and Plant Regeneration from Cotton Hypocotyl (*Gossypium Hirsutim* L.)", *Plant Physiology Supp.* (Apr. 1989) 89(4):8.
Gould et al., Regeneration of *Gossypium hirsutum* and *G. barbadense* from shoot apex tissues for transformation *Plant Cell Reports* (1991) 10(1):12–16.
Bhatt et al., "A Unified hormo–Nutritional Concept of Boll Shedding in Cotton", *Turrialba* (1982) 32(1):59–65.
Zimmerman et al., "Media and gelling agent efect on cotton callus initiation from excised seed hypocotyls", *Plant Cell, Tissue and Organ Culture* (1988) 15:269–274.
Finer et al. 1984. Plant Cell Reports 3:41–43.
Smith et al. 1977. In Vitro 13(5):329–334.

Primary Examiner—David T. Fox

[57] ABSTRACT

A method is provided for regenerating cotton plants from explant tissue. The improved method allows the generation of embryogenic callus from a cotton tissue explant which is not cultivated on cotton initiation media having exogenous plant hormones. The method can be utilized in the transformation of cotton plants, by cutting cotton tissue to form an explant, co-cultivating the cotton explant tissue with Agrobacterium comprising a DNA sequence of interest, and culturing the co-cultivated explant on cotton initiation media comprising a selective agent but having no exogenous plant hormones. In this fashion transformed cells are induced to produce embryogenic callus on hormone-free selective media.

10 Claims, 2 Drawing Sheets

COTTON TRANSFORMATION

FIELD OF THE INVENTION

This application relates to the field of plant genetics, in particular the transformation of cotton.

BACKGROUND OF THE INVENTION

Cotton is a plant of great commercial significance. In addition to the use of cotton fiber in the production of textiles, other uses of cotton include food preparation with cotton seed oil and animal feed derived from cotton meal and seed husks.

Despite the importance of cotton as a crop, the breeding and genetic engineering of cotton has taken place at a relatively slow rate because of the absence of reliable tissue culture methods capable of regenerating organized tissues, such as whole plants or shoots from cotton explants quickly or at a high frequency. Crop improvement is achieved with greater ease and rapidity when breeders are able to grow plant cells in tissue culture in such a way that whole plants, or portions thereof, can be rapidly produced from relatively high proportion of explants.

The regeneration of whole plants from an explant involves several growth stages. Typically, a tissue explant, having been excised from an adult plant or germinated seedling, is placed in a chemically defined medium under sterile conditions. By growing the explant under such controlled conditions for a period of time, an undifferentiated mass of cells, referred to as a callus, i.e., primary callus, may form.

By culturing this primary callus under the proper set of conditions, e.g., nutrients, light, temperature, humidity, and by providing the proper combination and concentration of plant growth regulators, the calli of some plant species have been induced to generate embryogenic callus which, in turn, can be induced to form somatic embryos in a process known as embryogenesis.

Somatic embryos are an organized mass of tissue that is similar to the embryo in a seed. Embryos formed by somatic embryogenesis and embryos in the seed both have the capacity to develop into a whole plant. The embryos formed by somatic embryogenesis are bipolar, containing meristem tissue at both root and shoot apices. Thus, upon the germination of somatic embryos, plantlets may be obtained.

The plant tissue culture literature describes several techniques for the generation of cotton callus, both embryogenic and non-embryogenic, and the production of embryonic tissue from cotton callus. These early experiments typically used explants derived from cotton seedling hypocotyls and cotyledons, and sequential transfers to plates containing callus initiation media.

Existing cotton somatic embryogenesis techniques have several shortcomings. The frequency with which embryogenesis occurs among the explants is typically low. Additionally, the techniques only work with a very limited number of cotton cultivars. Furthermore, most existing techniques for cotton somatic embryogenesis require extended periods of growth, i.e., usually more than 4 months, before somatic embryogenesis can take place.

Several advantages would arise from having the ability to induce embryogenesis (and thereby begin the process towards whole plants) directly and expeditiously from cotton explants placed on callus initiation medium. These advantages include a reduction in the amount of time required to reproduce plants via clonal propagation. This would allow rapid generation of genetic diversity through somaclonal variation, the production of pathogen free stock, and the propagation of rare or difficult to regenerate cotton varieties.

Relevant Literature

Price and Smith (1983) in *Handbook of Plant Cell Culture*, pages 487–510, provides a review of techniques used to obtain cotton calli.

Davidonis and Hamilton, in *Plant Sci. Letter* (1983) 32:89–93 reports somatic embryogenesis in cotton. The embryos developed after two years of growing callus in media containing naphthalene acetic acid (NAA) and kinetin. The explant was derived from *G. hirsutum L. cotyledons.*

U.S. Pat. No. 4,672,035 describes a method of regenerating cotton from *G. hirsutum L. callus* which has been first cultured in media containing naphthalene acetic acid (NAA) and kinetin and subsequently transferred to second media free of NAA and kinetin.

Shoemaker, et al., *Plant Cell Reports*, (1986) 3:178–181 describes cotton somatic embryogenesis from by calli derived from seedling hypocotyl explants of *G. hirsutum L.* grown on media containing NAA, kinetin, and adenine.

Firoozabady et al., *Plant Molecular Biology*, (1987) 10:105–116 describes the transformation of *G. hirsutum L.* seedling cotyledons by *A. tumefaciens*. Somatic embryogenesis is obtained from the calli derived form the transformed cotyledons.

U.S. Pat. Nos. 5,004,863, and 5,159,135 describe methods of transforming *G. hirsutum* seedling hypocotyl by co-cultivation with *A. tumefaciens* on media with hormones, auxins and cytokinins.

Trolinder and Goodin, *Plant Cell Reports* (1987) 6:231–234 describes the induction of somatic embryogenesis in calli initiated from seedling hypocotyls. The growth media used contained both auxins and cytokinins.

Trolinder and Goodin, *Plant Cell, Tissue and Organ Culture* (1988) 12:31–42 describes somatic embryogenesis in calli derived from explants prepared from the entire embryo axis of *G. hirsutum L.* mature derived seeds. The media employed contains both auxins and cytokinins.

Finer in *Plant Cell Reports*, (1988) 7:399–402 describes the production of embryo from callus suspension cultures in which the calli have been derived from seedling cotyledons of *G. hirsutum L.* The callus culture was established in a media comprising a synthetic auxin.

SUMMARY OF THE INVENTION

The present invention provides a mechanism for the regeneration of cotton plants via somatic embryogenesis from explants maintained continuously on culture medium which does not include growth regulating hormones. By comparison, when hormones are included in a culture medium with cotton tissue explants, as used in the prior art, cotton somatic embryogenesis is inhibited, or prevented in favor of undifferentiated primary callus formation.

Through continuous culture on hormone-free medium, and in contrast to culture on medium containing hormones, embryos are produced more rapidly, and a higher percentage of somatic embryos (per explant) are obtained. Additionally, the present invention finds application not only in cotton cultivars of the Coker type, and cultivars descended from Coker types. The present invention also enables somatic embryogenesis among other (non-Coker) cultivars that are non-regenerators under existing methods that include initial callus formation under conditions of hormone exposure.

Somatic embryogenesis on hormone-free tissue culture medium may provide several other advantages, including the more efficient production of transgenic plants from Coker, and Coker derived, cultivars, as well as the production of transgenic plants from an expanded number of cotton cultivars. In one preferred embodiment, cotton varieties which are difficult to regenerate by traditional techniques are induced to produce somatic embryos on hormone-free medium. The invention provides regenerable cotton strains of the Stoneville 84-828 variety.

The invention also provides a mechanism whereby tissues which are difficult to regenerate by traditional techniques may be induced to produce somatic embryos. In one preferred embodiment leaf tissue can be used to produce embryogenic callus and somatic embryos.

Another advantage of this invention is in reduced labor costs. Reductions in labor come from the reduced time-frame for transgenic cotton production, which lowers development costs of producing transgenic cotton cultivars in tissue culture.

A further benefit of the present invention is in a simplified method for screening cotton cultivars for regenerability, without multiple transfers of tissue following initiation. Under the present method results can be finalized in 12 weeks or less. In previous protocols using medium with hormones, such a screening would require at least one additional transfer of primary callus tissue to regeneration conditions, with up to 24 weeks necessary to complete the screening. Relative regenerability indicates which of several cotton cultivars can be used to efficiently produce transgenic plants, as well as how many explants are required to attain a target number of regenerated transgenic plants.

The invention allows alternative means of transformation (such as bombardment) to produce transformed plants of recalcitrant cultivars, by using hormone-free culture to obtain embryogenic tissue of recalcitrant cultivars, then transforming the embryogenic tissue via bombardment. Heretofore, only Coker, Coker-like cultivars, and lines of previously regenerated (R1S1) cultivars, have been transformed efficiently, due to the inability of other cultivars to regenerate under the standard protocol (Agrobacterium transformation, followed by culture of transgenic tissue on selective medium containing hormones, and plant regeneration on medium containing hormones, or substances with hormone-like effects (e.g., carbenicillin).

Prior to regeneration by the methods of this invention, transformation may be achieved. Several plant cell transformation techniques are available, including co-cultivation with *Agrobacterium tumefaciens*, microprojectile bombardment or the like. In the case of co-cultivation, the co-cultivation media is also preferably prepared without plant hormones.

DESCRIPTION OF THE PREFERRED EMBODIMENTS

A principal feature of the invention is the use of hormone free media to produce embryogenic callus directly from transformed cotton explants. Cotton is defined to be plant species belonging to the genus Gossypium, including interspecific and intercultivar crosses.

The tissue culture techniques presented are the only known techniques available for the generation of embryogenic callus and somatic embryos from cotton explants in culture without the application of exogenous plant growth regulators or hormones, such as auxins and cytokinins. While prior art methods are known to generate somatic embryos from embryogenic tissue, it was previously felt that it was necessary to first culture the explant tissue on a primary medium containing hormones to induce the formation of undifferentiated callus and after a period of time to transfer this callus to through a sequence of primary or secondary medium for a time sufficient to allow the appearance of embryogenic callus, after which the undifferentiated callus or embryogenic callus would be transferred to a secondary medium which does not contain hormones to encourage the formation of somatic embryos. The prior art methods have been unable to regenerate, via somatic embryogenesis, cultivars of cotton other than Coker (and cultivars descended from Coker).

Figure 1:
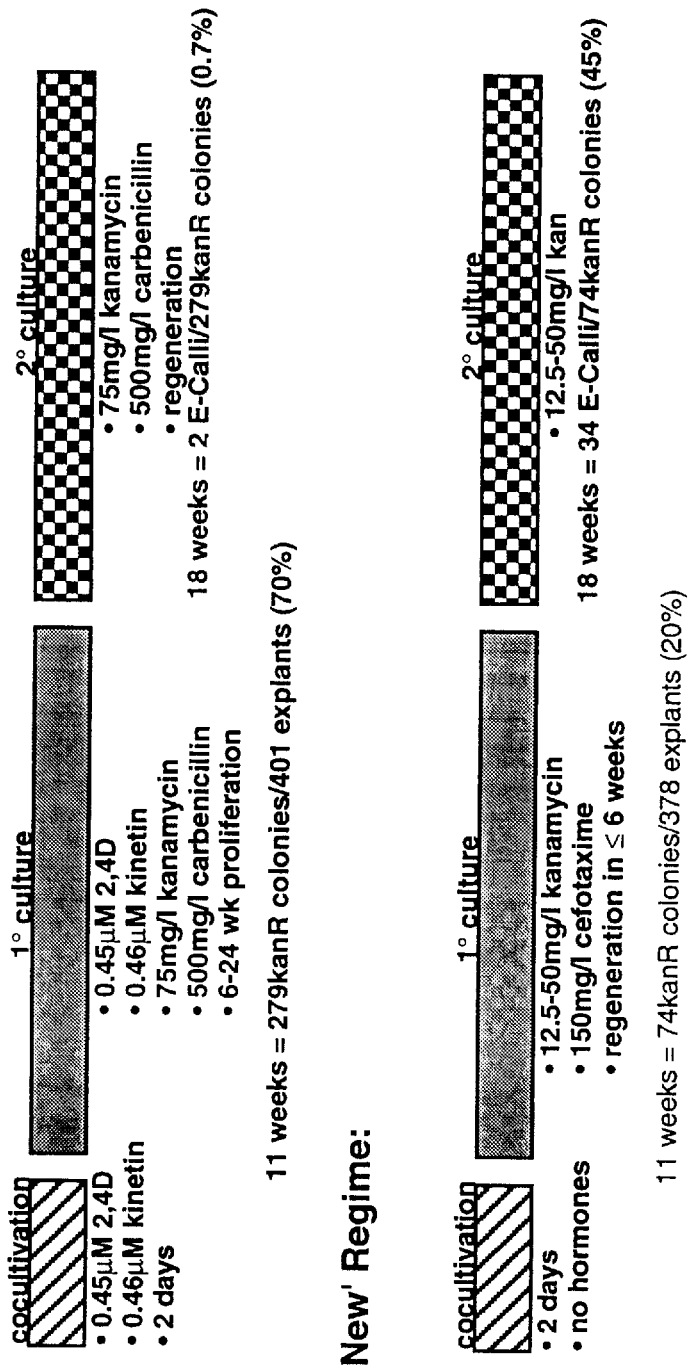
FIG. 1 is a schematic representation of the prior art regeneration methods, by the use of hormones, and the hormone-free method for attaining somatic embryogenesis of the present invention.

FIG. 1 provides a comparison of the known method for obtaining somatic embryos from cotton, which specifies the use of hormones for attaining somatic embryogenesis in cotton, with the hormone-free method of the present invention. In the new regime, cefotaxime is used rather than carbenicillin as carbenicillin shows some cyotkinin like effects.

One of the advantages of hormone free somatic embryogenesis is found in the reduced time for propagation of plants, as compared to known methods for callus formation which require a substantial growth period on hormone containing media during the formation of non-embryogenic, or undifferentiated primary callus. The present invention provides methods for inducing secondary embryogenic callus rapidly from the explant, reducing or eliminating the formation of non-embryogenic callus. By rapidly inducing embryogenic callus the labor of transferring non-embryogenic callus through stages of primary medium is avoided, as there is no need to induce and maintain a large amount of undifferentiated callus while waiting for embryogenic callus to arise.

A further advantage is the generation of embryogenic callus from a relatively high percentage of explants, and the more rapid formation of embryogenic callus. The presently disclosed method of somatic embryogenesis may be used with a wide variety of cotton cultivars, including cultivars that have hitherto resisted attempts to induce somatic embryogenesis.

Hormone-free medium is more conducive to embryogenesis, and the regeneration of some varieties is now possible where regeneration by traditional means is very low or non-existent. Thus, the present system adds some varieties to the list of cotton which can be transformed and regenerated into plants. Explants for use in the present invention may be derived from cultivars of cotton other than Coker, and Coker-derived cultivars.

Somatic embryos have even been obtained from Stoneville 84-828, a highly recalcitrant variety, indicating that this method is also applicable to a wide variety of cotton cultivars, including recalcitrant cultivars. By recalcitrant cotton cultivars is meant varieties which have not heretofore been amenable to somatic embryogenesis; i.e., cultivars other than Coker-type varieties.

The ability to transform cultivars other than Coker types may reduce labor and time-frames for developing transgenic cotton of commercial quality, by reducing the necessary number of backcrosses necessary in breeding the resulting transformed plant to a desired variety. With the ability to achieve somatic embryogenesis in an expanded range of cultivars, including non-Coker cultivars, an 'R1S1' (Regenerated once, Selfed once) strategy may be advantageously implemented for transformation of recalcitrant cultivars. An R1S1 strategy requires a broad ranger of regenerability, and a higher regeneration frequency such that many progeny of a selfed, regenerated plant may be obtained for any given cultivar. Increased somatic embryogenesis enables recovery of transgenic plants even from cultivars previously having a prohibitively low frequency of regeneration.

The conducive nature of hormone free regeneration also means that cotton plant tissues which have not been commonly utilized for regeneration can be now be used to produce somatic embryos. Leaf tissue are one example of a cotton tissue which has heretofore not been utilized in the regeneration of somatic embryos. The method is thus applicable to explants of numerous kinds of cotton tissue, including hypocotyl, leaf, root, petiole tissue and cotton embryos. Explant tissue is typically cut aseptically in order to avoid introducing bacteria or fungi into the plant culture media.

In a preferred embodiment, explants for use in the invention are obtained from expanding leaf or seedling hypocotyl tissue. Other preferred tissue for explants includes any cotton plant tissue comprising meristematic cells, such as sections of root tissue and leaf petiole tissue. Hypocotyl, leaf and root tissue contain meristematic cells in the cambium of the vascular system.

In both leaf and hypocotyl tissue it has been observed that callus formation appears to take place predominantly at the site of the vascular cambium. It has also be observed that in regeneration on hormone free medium callus tends to form predominantly at one end of hypocotyl tissue, with 80% to 90% of the callus forming at the basal end (towards root) of the hypocotyl section.

In experiments where the apical meristem is removed overnight prior to cutting of the explants, little or no regeneration is observed. On the other hand, when the apical meristem is left on hypocotyl explants, the explant has a tendency to form roots at the cut end, rather than embryogenic callus. Thus, hypocotyl explants for use in embryogenic callus formation on hormone free medium preferably lack the apical meristem region.

Since the apical meristem of plants produces indole acetic acid (IAA), also referred to as auxin, and IAA is transplanted downwards in the plant, it is possible that endogenous IAA plays a role in embryogenesis of cotton plants on hormone free medium. Plants also produce more IAA in the dark than in the light. In experiments where seedlings were grown variously in the dark and the light prior to cutting hypocotyl explants, those explants taken from plants grown in the light regenerated somatic embryos at a much lower frequency. In a preferred embodiment, then, cotton plants or seedlings are grown and maintained in the dark, at least for a period prior to cutting the explants.

After an explant is excised from the cotton plant, the explant is transferred to solid plant tissue culture medium suitable for the formation of embryogenic callus. Many of the basal salt/micronutrient solutions generally used in plant tissue cultures may be used to culture the explants derived from immature cotton embryos. Basal salt solutions that have been previously demonstrated to support the growth of cotton callus are preferred. The available literature, e.g., D.

Evans, R. Sharp, P. Ammirato, and Y. Yamata, *Handbook of Plant Cell Culture* (series of six volumes) Macmillian Publishing Company: Vol. 1 (1983), Vol. 2 (1984), Vol. 3 (1984), Vol. 4 (1986); McGraw Hill Publishing Company, Vol. 5 (1990) and Vol. 6 (1990); and T. Thorpe, *Plant Tissue Culture Methods and Applications in Agriculture*, Academic Press, Inc. (1981), disclose several basal salt and micronutrient solutions suitable for the growth of cotton callus tissue in vitro. Preferred basal salt/micronutrient solutions include Murashige and Skoog medium, Linsmaier and Skoog medium, Schenk and Hildebrandt medium, and Beasley and Ting medium. Particularly preferred for use as a basal salt solution is TRM medium, i.e., Murashige and Skoog medium with double $KNO_3$ concentration.

The tissue culture medium to which the explant is transferred will not contain any plant growth regulators. The subject invention differs substantially from earlier techniques for cotton somatic embryogenesis with respect to the lack of such growth regulators in the culture medium. Previously demonstrated techniques for obtaining cotton somatic embryogenesis have required that hormones, particularly cytokinins and auxins, be included in the growth medium. The medium employed in the present invention does not require the use of hormones, whether natural or synthetic. By using hormone free media as the primary medium, there is a more rapid formation of embryogenic callus than when hormones such as IAA (IAA), kinetin or 2,4 D are incorporated into the medium.

In prior techniques such cytokinins as 6-benzylamino purine (BAP), 2-isopentyladenine (2-ip), kinetin, 2-ip riboside and zeatin were commonly utilized for incorporation into the medium. Auxins commonly specified for cotton tissue culture medium include synthetic and natural auxins, such as IAA, NAA, 2,4 D, etc.

The culture media used for the generation of embryogenic callus from explants contains a gelling agent to solidify the medium. Gelling agents commonly used in plant tissue culture may be used in the culture medium employed in the present invention. Preferred gelling agents include the agar substitutes such as Phytagel™ (Sigma) and GelRite® (Merck and Co.).

In a most preferred embodiment, GelRite® (Scott Laboratories, Inc.) is utilized as the solidifying material in the regeneration medium, rather than agar. In many prior art regeneration methods a period of undifferentiated callus growth on hormone containing medium was used to successfully grow primary callus from the explant, in part due to the belief that the wound response of the explant tissue produced quantities of phenolic compounds which would inhibit embryogenesis. When utilizing GelRite®, there is an observed diminution of browning at the cut ends of the explant, indicative of a reduction in phenolic compounds.

The explants of this invention may be transformed by a variety of nucleic acid genetic constructs that are of use in genetically modifying plant cells. Transformation techniques of interest include co-cultivation with *Agrobacterium tumefaciens*, microprojectile bombardment and silicon carbide fiber-mediated transformation, for example. The manner of transformation is not critical to this invention.

DNA sequences of interest for transformation typically contain a nucleic acid sequence of interest fused to a regulatory sequence (promoter) capable of transcription or transcription and translation in plant cells. Sequences for transcription and translation (expression), will generally encode a polypeptide of interest. Polypeptides of interest may be polypeptides not naturally found in cotton cells or polypeptides naturally found in cotton cells. When sequences encoding polypeptides naturally found in cotton are present on a construct of interest, the promoter coupled with the sequence may be a promoter not naturally joined to the gene of interest. Polypeptides of interest include storage proteins, enzymes mediating herbicide resistance or pigment development, insecticidal proteins, mammalian regulatory proteins, plant regulatory proteins and cell wall proteins. Polypeptides for expression may also be modified so as to be targeted to organelles such as chloroplasts and mitochondria by means of adding the proper signal sequence. Sequences of interest may also include nucleic acid sequences encoding anti-sense RNA. Uses for anti-sense RNA include decreasing the expression of a gene and attenuating pathogen infections.

Promoters of interest may be either constitutive or inducible. Promoters may be expressed throughout the plant or in a tissue-specific manner.

In addition, genetic constructs for transformation preferably contain a selectable marker capable of being expressed in the transformation target cell and descendants thereof. Selectable markers permit cells containing a construct with a selectable marker to grow and divide under conditions that inhibit growth and replication of cells lacking the selectable marker. A variety of selectable markers are known to function in plant cells, these markers may be used in the transformation of cotton cells. Genetic markers of interest include resistance to G418, kanamycin, bromoxynil, hygromycin, methotrexate, gentamycin (gentamycin methyltransferase), glyphosate (EPSP synthase), and chlorsulfuron. As should be readily apparent, in some cases the polypeptide of interest may also be capable of functioning as a selectable marker. DNA sequences of interest may also contain vectors relevant to the particular transformation techniques to be employed and/or nucleotide sequences that permit the vector, or portions thereof, to be stably maintained within transformed cells.

Transformation of cotton by co-cultivation of *Agrobacterium tumefaciens* with *Gossypium hirsutum L. cotyledon* has been described by Firoozabady et al., *Plant Mol. Bio.* (1987) 10:105–116 and Umbeck et al., *Bio/Technology* (1987) 5:263–266. The transformation techniques described in Firoozabady et al. and in Umbeck et al. may be employed with the immature embryo explants of the present invention.

When introducing genetic constructs by *Agrobacterium tumefaciens* co-cultivation, the DNA sequence of interest will preferably contain a T-DNA sequence, preferably a disarmed T-DNA sequence, to promote integration of the vector into the cotton genome. In particular, the use of at least a right T-DNA border region and preferably both a right and left T-DNA border region is preferred.

Cotton explants may also be transformed by bombardment with microprojectiles coated with a genetic construct of interest. Details about the transformation of plant cells by microprojectile bombardment is described in generally available literature, e.g., Klein et al., *Nature* (1988) 327:70–73. Cells of the cotton explants chosen for regeneration by the present invention may be transformed by employing essentially the same bombardment techniques used to transform other plant cells.

Embryogenic callus may be readily distinguished from the non-embryogenic callus, i.e., primary callus, on the basis of appearance. Embryogenic callus cells are usually small in size, cream-yellow in color, and organized into embryo or pre-embryo structures, whereas primary callus is predominantly green or white and disorganized with large vacuolated cells.

Embryogenic callus may be excised from the primary callus on which it arose and subsequently be propagated for extended periods of time either in solid tissue culture or in suspension tissue culture by employing tissue culture techniques generally known to those skilled in the art. When desired, the embryos may be allowed to convert, i.e., germinate, and form whole plants.

In order to regenerate whole plants, somatic embryos may be excised from embryogenic callus and subsequently transferred to tissue culture growth medium designed to facilitate the formation of roots by methods familiar to those in the art. Rooted shoots may be subsequently transferred to growth in soil when desired.

When regeneration is preceded by transformation of explants with a transformation construct containing a selectable marker, the explants are subsequently cultured in media either under selective pressure or not under selective pressure for the marker present on the genetic construction. In some cases the sequence of interest can act as the selectable marker. By selective pressure, it is intended that the cells in culture be exposed to an environmental factor, usually chemical, that favors the growth and/or survival of cells expressing the selection marker. The level of selective pressure may be varied at different stages during the process of producing embryos from the explant. For example, an explant transformed with a vector containing a neomycin phosphotransferase may be placed on a low level selection media containing 5–75 mg/ml kanamycin immediately after transformation and subsequently transferred to a high level selection media containing 75–200 mg/ml kanamycin after embryogenic callus buds have formed.

By altering the timing and the level of selective pressure applied to the tissue in culture, it may be possible to exert control over the proportion of transformed cells present in the resultant callus. In general, the earlier in the tissue culture process the selective pressure is applied and the greater the selective pressure that is applied, the greater the percentage of transformed cells present in the callus. Selective pressure may be applied at one or more stages of the plant's growth.

When explants suitable for the development of embryogenic callus are grown under conditions for the formation of embryogenic callus, selective pressure is preferably continuous, although alternatively it may be applied either before or after the embryogenic callus has formed once cells have been transformed. Selective pressure may be applied when the embryogenic callus is transferred to fresh medium. Similarly, selective pressure may also be applied after embryos are transferred to embryo pulse medium, or germination medium. Selective pressure may also be applied as somatic embryos are rooted and after embryos have formed whole plants.

When co-cultivating with the present invention it is also not necessary that the explant be placed onto "feeder plates". Feeder plates are petri plates containing initiation medium with cytokinin and a layer of tobacco feeder cells. With the present invention a sterile filter paper Whatman #1 is simply placed over the surface of the callus initiation medium, which appears to function in keeping Agrobacterium growth to a minimum.

The invention having been described, the following examples are offered to illustrate the subject invention by way of illustration, not by way of limitation.

EXAMPLE 1

Explant Preparation

Coker 315 seeds were surface disinfected by placing in 50% Clorox® (2.5% sodium hypochlorite solution) for 20 minutes and rinsing 3 times in sterile distilled water. Following surface sterilization, seeds were germinated in 25×150 sterile tubes containing 25 mls ½×MS salts: ½×B5 vitamins: 1.5% glucose: 0.3% GelRite. Seedlings were germinated in the dark at 28° C. for 7 days. Hypocotyls were excised from eight day old seedlings, cut into 0.5–0.7 cm sections and placed onto sterile filter papers placed over a petri plate containing Callus Initiation Medium (CIM) without hormones. The components of CIM are provided in Table 1.

TABLE 1

| Concentrations | Compound | Source |
| --- | --- | --- |
| 1 X | Murashige and Skoog Salts | Gibco |
| 30 g/L | glucose | Mallinckrodt |
| 100 mg/L | myo-inositol | Sigma |
| 1 mg/L | nicotinic acid | Sigma |
| 1 mg/L | pyridoxine HCL | Sigma |
| 10 mg/L | thiamine-HCL | J. T. Baker |
| 1.87 g/L | magnesium chloride | Sigma |
| 1.90 g/L | potassium nitrate | Sigma |
| 4 g/L | GelRite ® | Scott Lab., Inc. |

Hormone-containing medium ('CIM-3') is the same as provided in the above table, only it contains hormones at the following levels: 0.45 $\mu$M 2,4 D & 0.46 $\mu$M kinetin.

EXPERIMENT 2

Embryogenesis on Hormone Free Medium

Explant tissue was prepared as in Example 1 and incubated at 28+2° C., 30 uE 16 hours:8 hours light:dark period. Various explants were incubated on hormone-free medium, or on some combination of an initial period of incubation on CIM-3 followed by a transfer to hormone free medium.

Figure 2:
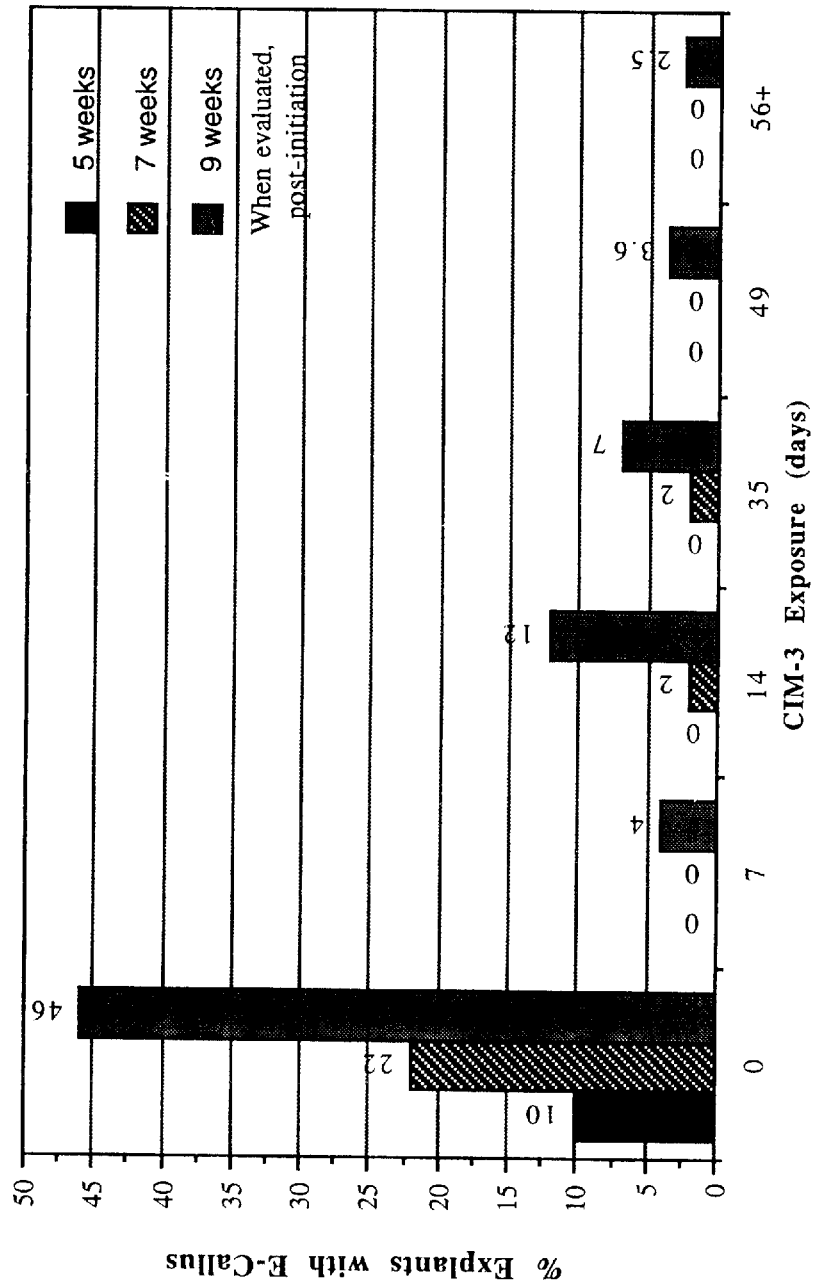
FIG. 2 is a graphical representation of data showing the effect of the time of exposure of callus initiation medium containing hormones on regeneration in cotton.

At 5, 7 and 9 weeks embryogenic callus was identified. FIG. 2 illustrates the improvement in the percentage of embryogenesis following continuous culture on hormone free medium ('0'), compared to exposure for any length of time to a hormone-containing medium (CIM-3).

In addition to the increased percent regeneration (embryogenic calli) by 9 weeks, the rapidity with which embryogenic callus formed was increased: 10% (10/100) of explants that were cultured continuously on hormone-free medium had formed embryogenic callus by the time of the first observation at 5 weeks, whereas none of the explants exposed to hormone-containing medium for any length of time had formed embryogenic callus. After 9 weeks, only 2.5% (3/116) of explants exposed continuously to hormone-containing medium had developed embryogenic callus, compared to 46% (46/100) of explants cultured continuously on hormone-free medium.

EXPERIMENT 3

Recovery of Embryogenic Callus from Stoneville 506

Stoneville 506 is a recalcitrant cultivar which rarely undergoes somatic embryogenesis under conditions that include hormones. However, after 14 weeks of continuous culture on hormone-free medium, 2 embryogenic callus colonies were recovered from 53 hypocotyl explants of ST506 (each explant was from a different seedling). The recovery of embryogenic calli from this recalcitrant cultivar was dependent upon the hormone-free culture regime, illustrated by the fact that no embryogenic callus was observed among 420 explants that had been exposed to hormone-containing medium for as little as one day, or up to 14 weeks.

EXPERIMENT 4

Expansion of Cultivars that Regenerate

Eight cotton cultivars were subjected to a screen of regenerability. At twenty four months cultivars capable of somatic embryogenesis on hormone containing medium, namely C130, C320, and Georgia King, had relative regenerability on hormone-free medium, as a percentage of E-callus formed, of 71%, 81%, and 58%, compared to callus formed on continuous hormone-containing medium. The lowest regeneration occurred in cultures transferred after six weeks from hormone-containing medium to hormone-free medium. Within a given culture regime and cultivar each explant was taken from a different seedling.

The results are shown in Table 2. Results are given as number of E-calli/number of explants (%).

TABLE 2

| CULTIVAR | continuous hormones | hormone initiation, transfer to ∅ hormone | continuous without hormone |
| --- | --- | --- | --- |
| C130 | 38/90 (42%) | 22/120 (18%) | 36/120 (30%) |
| C320 | 25/90 (28%) | 23/120 (19%) | 27/120 (23%) |
| GA King | 13/91 (14%) | 7/118 (5.9%) | 10/120 (8.3%) |
| 9358 | 2/88 (2.3%) | 1/119 (0.8%) | 3/120 (2.5%) |
| 84–828 | 0/91 | 0/115 | 2/120 (1.7%) |
| KC311 | 0/89 | 0/119 | 0/119 |
| ST132 | 0/90 | 0/120 | 0/120 |
| LA887 | 0/90 | 0/120 | 0/115 |

Explants under this regime were transferred once after four weeks onto fresh medium of the same composition, and were at that tame reduced from 4 colonies per plate to 2 colonies per plate.

The regime designated 'hormone initiation, transfer to ∅ hormone' included six weeks on MS salts, 3% glucose, 0.45 $\mu$M 2,4 D and 0.46 $\mu$M kinetin, followed by the remainder of the period on MS salts modified by addition of 1.9 g/l $KNO_3$, 3% glucose, and no hormones. Colonies were subcultures of calli from the 'continuous hormones' regime, and were inoculated at 2 per plate after the initial 6 week period.

The regime designated 'continuous without hormones' included MS salts modified by addition of 1.9 g/l $KNO_3$, 3% glucose, and no hormones. Explants under this regime remained on the initial medium at 4 colonies per plate, and were never transferred to fresh medium.

These results demonstrate and increased ability to regenerate certain recalcitrant cotton varieties on hormone free medium. The 84-828 cultivar formed embryogenic callus only on the continuous hormone-free regime.

EXPERIMENT 5

Reduced Regeneration Time

Elapsed time from initiation until E-callus formation was reduced by continuous culture on hormone-free medium. Table 3 provides a summary of data taken at twelve weeks on hormone-containing medium.

TABLE 3

| Cultivars | continuous hormones | hormones (6 weeks) then no hormones | continuous no hormones |
|---|---|---|---|
| Coker 320 | 1/90 | 3/120 | 18/120 |
| Coker 130 | 4/90 | 7/120 | 33/120 |
| Georgia King | 0/91 | 3/120 | 8/120 |
| 9358 | 0/90 | 0/120 | 2/120 |
| 84–828 | 0/90 | 0/120 | 1/120 |

All publications and patent applications mentioned in this specification are indicative of the level of skill of those skilled in the art to which this invention pertains. All publications and patent applications are herein incorporated by referenced to the same extent as if each individual publication or patent application was specifically and individually indicated to be incorporated by reference.

EXPERIMENT 6

Increase in Embryogenesis

Table 4 summarizes the experimental evidence from two separate trials that embryogenic callus regeneration for transformed cotton tissue is improved by culture which excludes exposure to exogenous hormones.

TABLE 4

Trial A

| Transformation Protocol* | Number of explants initiated | Number of kanamycin tolerant E-calli at 16 weeks | Number of kanamycin tolerant E-calli at 20 weeks |
|---|---|---|---|
| With Hormones | 860 | 24 (1.3%) | 65 (7.5%) |
| Without Hormones | 855 | 108 (12.6%) | 109 (12.7%) |

Trial B

| Transformation Protocol* | Number of explants initiated | Number of kanamycin tolerant E-calli at 16 weeks | Number of kanamycin tolerant E-calli at 18 weeks |
|---|---|---|---|
| With Hormones | 540 | 0 | 22 (4.0%) |
| Without Hormones | 525 | 48 (9.1%) | 58 (11.0%) |

In the above table, the protocol 'With Hormones' includes 6–10 weeks of explant culture on Callus Initiation Medium with 0.45 μM 2,4-D and 0.46 μM kinetin. The protocol 'Without Hormones' indicates continuous explant culture on Regeneration Medium, which does not contain hormones. Both protocols used transformation via *Agrobacterium tumefaciens* cocultivation and selection on medium containing kanamycin.

Although the foregoing invention has been described in some detail by way of illustration and example for purposes of clarity of understanding, it will be obvious that certain changes and modifications may be practiced within the scope of the appended claim.

What is claimed is:

1. In a method for regenerating transformed cotton plants from explant tissue, the improvement whereby embryogenic callus is generated from a transformed cotton tissue explant which is cultivated on cotton callus initiation media which is not supplied with exogenous plant hormones, wherein said explant tissue is hypocotyl tissue cut from a seedling which has been grown in the dark.

2. The method according to claim 1 wherein said explant tissue is co-cultivated with Agrobacterium prior to regeneration on hormone-free medium.

3. A method according to claim 2 wherein said Agrobacterium comprises a DNA sequence of interest.

4. A method according to claim 2 wherein said DNA sequence of interest comprises a selectable marker.

5. A method according to claim 1 wherein said explant is transformed by bombarding said explant with particles coated with a DNA sequence of interest.

6. A method according to claim 5 wherein said DNA sequence of interest comprises a selectable marker.

7. A method according to either one of claim 2 or claim 5 comprising further culturing said embryogenic tissue to form a somatic embryo.

8. A method for the transformation of cotton plants, said method comprising the steps of cutting cotton hypocotyl tissue to form an explant, wherein said hypocotyl tissue is cut from seedling which has been grown in the dark, co-cultivating said cotton explant tissue with Agrobacterium comprising a DNA sequence of interst, and culturing said co-cultivated explant on cotton callus initiation media comprising a selective agent and no exogenous plant hormones, whereby transformed cells are induced to produce embryogenic callus on said hormone-free selective media.

9. The method according to claim 8 wherein said DNA sequence of interest comprises a selectable marker which permits said transformed embryogenic callus cells to grow on said hormone-free selective media.

10. A method according to claim 8 further comprising the step of culturing said embryogenic callus in the presence of said selective agent to form a transformed somatic embryo.

* * * * *